(12) United States Patent
Natale et al.

(10) Patent No.: US 9,023,092 B2
(45) Date of Patent: May 5, 2015

(54) ENDOSCOPES ENHANCED WITH PATHOGENIC TREATMENT

(71) Applicants: Anthony Natale, New Preston, CT (US); David Muller, Boston, MA (US)

(72) Inventors: Anthony Natale, New Preston, CT (US); David Muller, Boston, MA (US)

(*) Notice: Subject to any disclaimer, the term of this patent is extended or adjusted under 35 U.S.C. 154(b) by 0 days.

(21) Appl. No.: 13/839,383

(22) Filed: Mar. 15, 2013

(65) Prior Publication Data

US 2013/0274549 A1  Oct. 17, 2013

Related U.S. Application Data

(63) Continuation-in-part of application No. 13/592,883, filed on Aug. 23, 2012, now Pat. No. 8,668,727.

(60) Provisional application No. 61/526,346, filed on Aug. 23, 2011.

(51) Int. Cl.
| | | |
|---|---|---|
| *A61N 5/06* | (2006.01) | |
| *A61B 18/18* | (2006.01) | |
| *A61B 1/018* | (2006.01) | |
| *A61B 1/015* | (2006.01) | |
| *A61M 5/00* | (2006.01) | |
| *A61B 1/307* | (2006.01) | |
| *A61B 1/233* | (2006.01) | |

(Continued)

(52) U.S. Cl.
CPC ............... *A61N 5/062* (2013.01); *A61B 1/018* (2013.01); *A61B 1/015* (2013.01); *A61M 5/00* (2013.01); *A61N 5/0603* (2013.01); *A61B 1/07* (2013.01); *A61B 1/307* (2013.01); *A61B 1/233* (2013.01); *A61B 1/2676* (2013.01); *A61B 1/317* (2013.01); *A61B 1/3132* (2013.01); *A61B 1/273* (2013.01); *A61B 1/31* (2013.01); *A61N 5/0624* (2013.01); *A61N 2005/063* (2013.01); *A61N 2005/0661* (2013.01); *A61B 18/24* (2013.01); *A61B 2018/00982* (2013.01)

(58) Field of Classification Search
CPC .............................. A61N 5/062; A61N 1/368
USPC ............................................. 607/88, 9; 606/9
See application file for complete search history.

(56) References Cited

U.S. PATENT DOCUMENTS

| | | |
|---|---|---|
| 5,100,429 A | 3/1992 | Sinofsky et al. |
| 6,224,893 B1 | 5/2001 | Langer et al. |

(Continued)

FOREIGN PATENT DOCUMENTS

| | | |
|---|---|---|
| EP | 1054642 B1 | 5/2008 |
| EP | 2380535 A1 | 10/2011 |

(Continued)

OTHER PUBLICATIONS

International Search Report and Written Opinion mailed Dec. 21, 2012 for International Application No. PCT/US2012/052008 (9 pages).

(Continued)

*Primary Examiner* — Lynsey Crandall
*Assistant Examiner* — Sebastian X Lukjan
(74) *Attorney, Agent, or Firm* — Morgan, Lewis & Bockius LLP

(57) ABSTRACT

Various endoscopes are integrated with an applicator configured for delivering a therapeutic solution to an internal anatomic target that may be infected by pathogenic microorganisms and a UV light-emitting device transmitting UV light thereto.

26 Claims, 16 Drawing Sheets

(51) Int. Cl.
*A61B 1/267* (2006.01)
*A61B 1/317* (2006.01)
*A61B 1/313* (2006.01)
*A61B 18/24* (2006.01)
*A61B 1/07* (2006.01)
*A61B 1/273* (2006.01)
*A61B 1/31* (2006.01)
*A61B 18/00* (2006.01)

(56) References Cited

U.S. PATENT DOCUMENTS

| | | | |
|---|---|---|---|
| 6,454,790 B1* | 9/2002 | Neuberger et al. | 607/88 |
| 2002/0192289 A1 | 12/2002 | Zheng et al. | |
| 2003/0224002 A1 | 12/2003 | Hasan et al. | |
| 2004/0230156 A1 | 11/2004 | Schreck et al. | |
| 2006/0135644 A1 | 6/2006 | Engelbrecht et al. | |
| 2006/0167531 A1 | 7/2006 | Gertner et al. | |
| 2008/0014248 A1* | 1/2008 | Park et al. | 424/436 |
| 2008/0221647 A1* | 9/2008 | Chamberland et al. | 607/88 |
| 2008/0255549 A1* | 10/2008 | Rose et al. | 606/15 |
| 2009/0028946 A1 | 1/2009 | Sheardown et al. | |
| 2009/0171305 A1 | 7/2009 | El Hage | |
| 2009/0238778 A1 | 9/2009 | Mordas et al. | |
| 2010/0057060 A1 | 3/2010 | Herekar | |
| 2010/0234793 A1 | 9/2010 | Dacey, Jr. et al. | |
| 2010/0318017 A1 | 12/2010 | Lewis et al. | |
| 2011/0060267 A1 | 3/2011 | DeWoolfson et al. | |
| 2011/0085991 A1 | 4/2011 | Giniger | |
| 2011/0190742 A1 | 8/2011 | Anisimov | |
| 2011/0238002 A1* | 9/2011 | Kurkayev | 604/21 |
| 2011/0280763 A1 | 11/2011 | Trokel et al. | |
| 2011/0282333 A1 | 11/2011 | Herekar et al. | |
| 2012/0065465 A1* | 3/2012 | Kucklick | 600/104 |
| 2012/0065572 A1 | 3/2012 | Lewis et al. | |
| 2012/0121567 A1 | 5/2012 | Troisi et al. | |

FOREIGN PATENT DOCUMENTS

| | | |
|---|---|---|
| KR | 20100005924 U | 6/2010 |
| RU | 2345738 C1 | 2/2009 |
| WO | WO-0078393 A1 | 12/2000 |
| WO | WO-0167878 A1 | 9/2001 |
| WO | WO-0187416 A1 | 11/2001 |
| WO | WO-03084601 A2 | 10/2003 |
| WO | WO-2007025244 B1 | 12/2007 |
| WO | WO-2008064904 A1 | 6/2008 |
| WO | WO-2008095148 A3 | 3/2009 |
| WO | WO-2009029049 A8 | 6/2009 |
| WO | WO-2009073213 A1 | 6/2009 |
| WO | WO-2011050164 A1 | 4/2011 |
| WO | WO-2011019940 A3 | 6/2011 |
| WO | WO-2011094758 A2 | 8/2011 |
| WO | WO-2012047307 A1 | 4/2012 |
| WO | WO-2012095876 A1 | 7/2012 |
| WO | WO-2012095877 A1 | 7/2012 |
| WO | WO-2012078980 A3 | 9/2012 |
| WO | WO2013028833 A1 | 2/2013 |

OTHER PUBLICATIONS

Notification Concerning Payment of Prescribed Fees of PCT/US2012/052008 dated Aug 29, 2012 (2 pages).

* cited by examiner

ENDOSCOPES ENHANCED WITH PATHOGENIC TREATMENT

CROSS-REFERENCE TO RELATED APPLICATION

This is a continuation-in-part of U.S. patent application Ser. No. 13/592,883, which was filed on Aug. 23, 2012 and which claims priority to and the benefit of U.S. Provisional Patent Application No. 61/526,346, which was filed on Aug. 23, 2011. The foregoing applications are incorporated herein by reference in their entireties.

FIELD OF THE INVENTION

In various embodiments, the present invention relates generally to endoscopes having the ability to treat maladies caused by pathogenic microorganisms.

BACKGROUND

Endoscopes are instruments used to examine the interior of a hollow organ or a cavity of the body in order to minimize invasive surgeries. Endoscopes are often employed as disease-diagnosis tools; for example, a gastrointestinal (GI) endoscope and a cystoscope can visualize a patient's GI tract and urinary tract to diagnose, respectively, an unexplained diarrhea or hematuria. In addition, endoscopes may be combined with a variety of surgical instruments to enable surgeons to perform procedures, such as orthopedic implantations, while imaging the region of interest using video, ultrasound, laser, optics or other imaging modalities.

Conventionally, both diagnostic and surgical endoscopes assist in examination of interior body regions only; actually treating disease may require another separate procedure. As a result, patients must often make repeated clinic visits with attendant inconvenience and delays, risking not only increased mental anxiety but also complications associated with progressing symptoms. In addition, the use of endoscopes may result in injury to or pathogenic infections at the surgical site (e.g., the implantation site), a consideration that limits use of endoscopic examination as an adjunct to treatment.

Consequently, there is a need for a system and a method that can combine endoscopic examination with therapy. In addition, it is desirable for such a system and method to be associated with a reduced risk of pathogenic infections that can result from endoscope usage.

SUMMARY

In various embodiments, the present invention combines endoscopic imaging with systems and methods for treating maladies caused by pathogenic microorganisms; this allows physicians to image the target region and conduct treatment immediately, if necessary. In addition, the combined system provides a preventive treatment during surgery (e.g., an orthopedic implantation) to reduce or eliminate the risk of postoperative infection at the surgical site. In one implementation, the combined system, including a pathogenic treatment device and an endoscope (such as a GI endoscope, a cystoscope, a nasopharyngoscope, a bronchoscope, an arthroscope, or a laparoscope), delivers riboflavin to selected anatomical target regions (such as the GI track, bladder, paranasal sinus cavities, oral cavity, lungs, joint spaces, surfaces of orthopedic implants, or an abdominal cavity) and concurrently or sequentially exposes the target regions to ultraviolet (UV) light (of a specific wavelength, peak wavelength, or wavelength band) to activate the riboflavin and produce an antimicrobial effect while the target regions are imaged. The combined system permits simultaneously assessing and treating the target area, thereby effectively reducing the infectious pathogen without complications or side effects associated with typical endoscopic examinations. Additionally, devices in accordance with the combined endoscope and pathogenic treatment device are advantageously inexpensive and easy to operate.

Accordingly, in one aspect, the invention pertains to a system capable of examining an internal anatomical target in a patient's body and treating pathogenic infections therein. In various embodiments, the system includes an endoscope for examining the internal anatomical target, a device for emitting actinic radiation (e.g., a UV radiation source) via an emission channel, and an applicator including a reservoir for a radiation-activatable biocidal fluid and a fluidic channel. In some embodiments, an output of the emission channel and a fluidic outlet of the fluidic channel are configured for accessing the internal anatomical target and delivering both actinic radiation and the radiation-activatable biocidal fluid (e.g., a riboflavin solution or a riboflavin-derivative solution) thereto without interfering with operation of the endoscope. The endoscope, device and the applicator may be integrated into a single assembly. Alternatively, the endoscope may be configured to enter a first surgical port and the light output and the fluidic outlet are configured to enter a second surgical port spaced apart from the first surgical port. In one implementation, the system further includes a supply of the radiation-activatable biocidal fluid in the fluid reservoir for delivery to the internal anatomical target via the fluidic channel.

The endoscope may be a gastrointestinal endoscope, including one or more working channels and one or more optical channels for guiding light to the internal anatomical target. The working channel(s) may be the fluidic channel and the optical channel(s) may be the emission channel. In addition, the emission channel and the fluidic channel may be disposed within the working channel(s) of the gastrointestinal endoscope.

The endoscope may be a cystoscope, including a first channel for providing images of the internal anatomical target and a second channel for allowing fluids to be instilled into the internal anatomical target. In one embodiment, the first channel is the emission channel and the second channel is the fluidic channel. In another embodiment, the emission channel and the fluidic channel are inserted in the second channel of the cystoscope.

The endoscope may be a nasopharyngoscope, including an optical channel for guiding light to the internal anatomical target. The system may further include a sleeve surrounding one or more portions of the nasopharyngoscope to create a channel between the sleeve and an outer surface of the nasopharyngoscope. In one embodiment, the created channel is the fluidic channel and the optical channel is the emission channel. In another embodiment, the created channel is the fluidic channel and the emission channel.

The endoscope may be a bronchoscope, including one or more working channels and one or more optical channels. In one embodiment, the working channel(s) is the fluidic channel and the optical channel(s) is the emission channel. In another embodiment, the emission channel and the fluidic channel are inserted in the working channel(s) of the bronchoscope.

The endoscope may be an arthroscope, including a trocar having a lumen for guiding light to the internal anatomical target. In one embodiment, the emission channel and the fluidic channel are inserted in the lumen of the trocar. In another embodiment, the system further includes a sleeve surrounding one or more portions of the trocar to create a channel between the sleeve and an outer surface of the arthroscope. The created channel is the fluidic channel and the emission channel.

The endoscope may be a laparoscope, including a trocar having an optical channel for guiding light to the internal anatomical target. In some embodiments, the emission channel and the fluidic channel are inserted in the optical channel of the trocar. In addition, the system may further include a sleeve surrounding one or more portions of the trocar to create a channel between the sleeve and an outer surface of the laparoscope. In one embodiment, the created channel is the fluidic channel and the optical channel is the emission channel. In another embodiment, the created channel is the fluidic channel and the emission channel.

In another aspect, the invention relates to a method for examining an internal anatomical target in a patient's body and treating pathogenic infections therein. In various embodiments, the method includes inserting an endoscope adjacent to or into the internal anatomical target; capturing an image of the target via the endoscope; while capturing the image and without interfering therewith, delivering a radiation-activatable biocidal solution (e.g., a riboflavin solution or a riboflavin-derivative solution) to the target; and exposing the target to actinic radiation (e.g., UV radiation) to activate the radiation-activatable biocidal solution.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The terms "substantially" and "approximately" mean±10% and, in some embodiments, ±5%. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
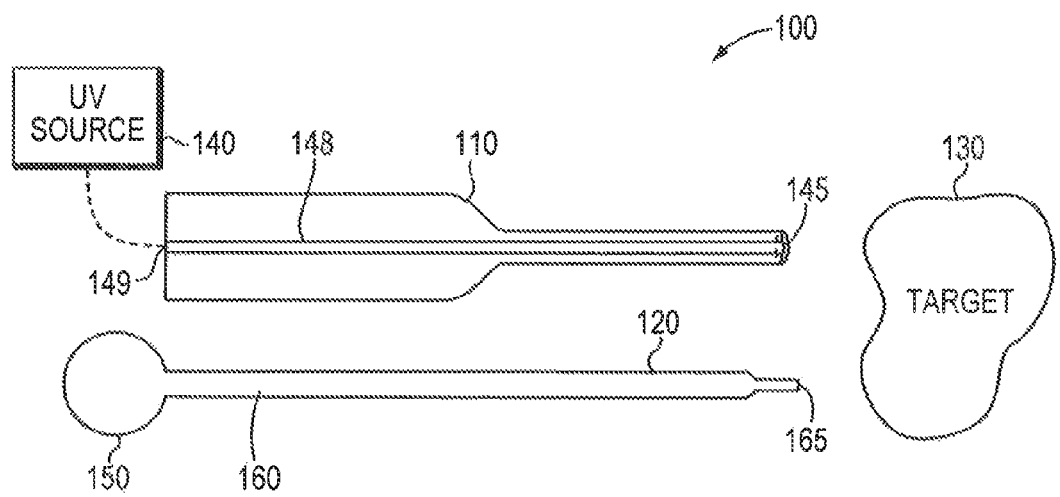
FIG. 1A schematically illustrates a riboflavin solution applicator separate from a UV light-emitting device in accordance with embodiments of the current invention.
Figure 1B:
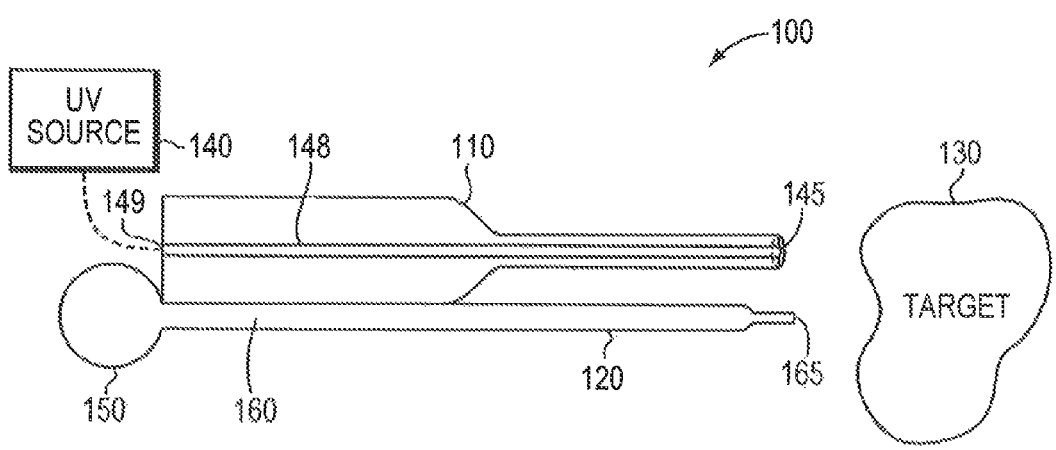
FIGS. 1B and 1C schematically illustrate a riboflavin applicator and a UV light-emitting device combined in a single handheld wand in accordance with embodiments of the current invention.
Figure 1C:
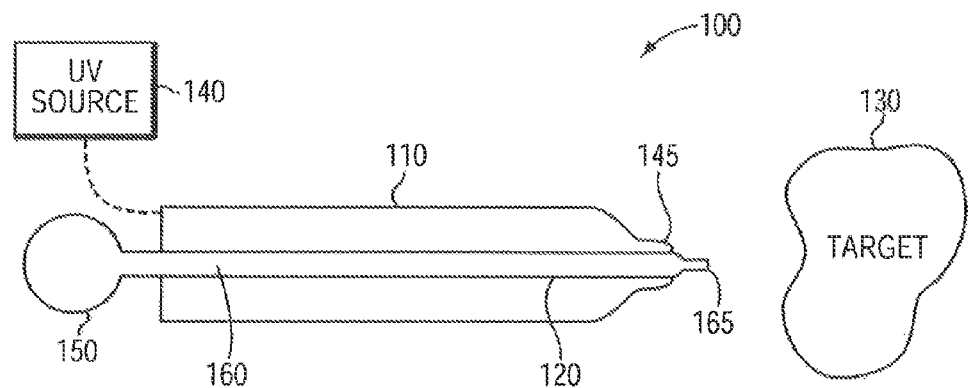

In various embodiments, as illustrated in FIGS. 1A, 1B, and 1C, a system 100 in accordance herewith comprises an actinic-radiation device (e.g., UV light-emitting device) 110 and an applicator 120 for delivering a radiation-activatable biocidal solution (e.g., a riboflavin solution or a riboflavin-derivative solution) to a target region 130 that is infected by pathogenic microorganisms. As used herein, the term "radiation" broadly connotes any electromagnetic radiation and the term "actinic radiation" connotes any radiation that chemically activates a substance of interest—e.g., in the case of riboflavin and its derivatives, UV radiation. Solely for ease of discussion, the actinic-radiation device hereafter is assumed to be a UV light-emitting device, and the radiation-activatable biocidal solution hereafter is assumed to be a riboflavin solution, but those of skill in the art will recognize that other suitable biocides activatable by radiation may be employed. The target region 130 is typically an internal anatomic region that is difficult to access. In one embodiment, the riboflavin solution applicator 120 is separate from the UV light-emitting device 110 (FIG. 1A), while in another embodiment, the riboflavin applicator 120 and the UV light-emitting device 110 are combined in a single handheld wand (FIGS. 1B and 1C). The UV light-emitting device 110 is designed to emit a specific wavelength, peak wavelength, or wavelength band (e.g., 340-400 nm) of UV light and to direct the light to the target region 130. In one embodiment, the entire or partial target region that the riboflavin solution is applied thereon is exposed to the emitted UV light. A UV light source 140 that may be located within the UV light-emitting device 110 or may be separate transmits light to the end face 145 of the device 110 via, for example, one or more optical fibers 148. The UV light source is conventional and may be, for example, one or more light-emitting diodes, one or more UV lasers, an incandescent source, etc. The light source 140 may include a suitable power supply (e.g., a battery or circuit that takes power from the AC mains), or may instead include a connector that may be received by a suitable external power supply. Typically the light source 140 will include suitable focusing optics, e.g., for concentrating light onto the proximal end face 149 of an optical fiber 148 for emission at the distal end face 145.

Figure 1D:
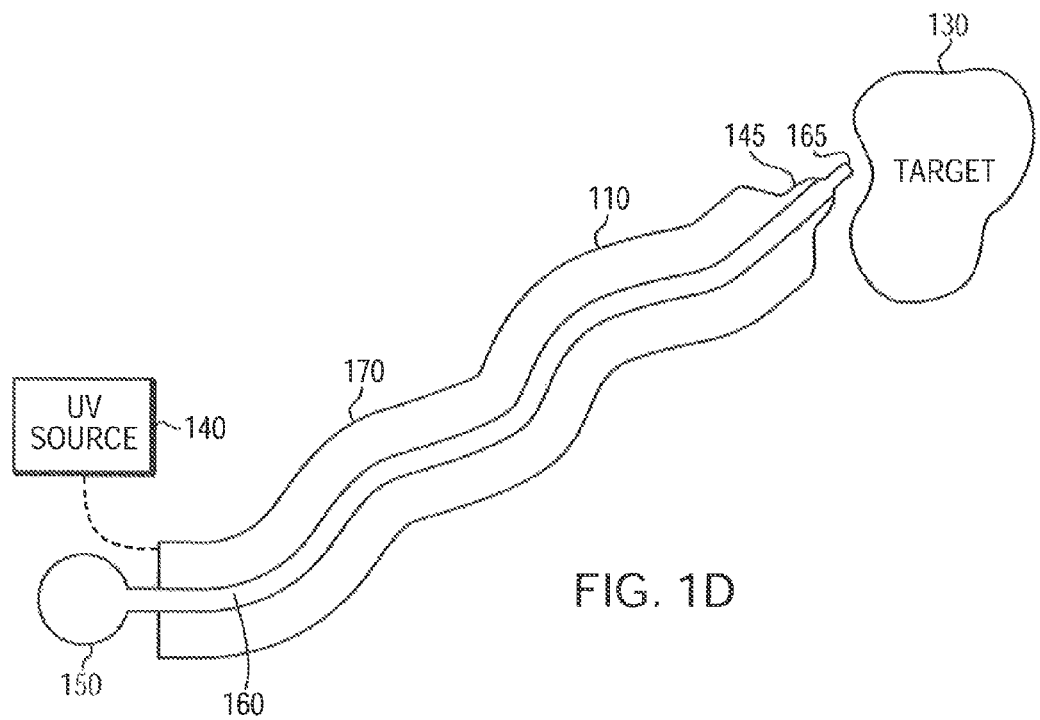
FIG. 1D schematically illustrates delivery ends and/or delivery elements of the UV light-emitting device and the applicator curved or shaped to provide access to the target tissue.

The riboflavin applicator 120 includes a fluid reservoir 150 for storing the riboflavin solution and a delivery element 160 for attaining physical access to the targeted tissue 130 and facilitating delivery of riboflavin thereto. The opening 165 on the tip of the delivery element 160 to the target region 130 may be a simple orifice or the open end of a hollow tube, or may incorporate conventional structures and/or elements for spraying, aerosolizing, misting, and/or causing the riboflavin solution to form small droplets to facilitate delivery over a larger surface area than would be possible with only a simple opening. The delivery ends 145, 165 and/or the delivery elements 170, 160 of the UV light-emitting device 110 and the applicator 120, respectively, may be curved or otherwise shaped in the manner of a surgical instrument (FIG. 1D), and may include a blade, cutter or other access-providing element, which may be retractable. The delivery ends and/or elements may be permanently shaped to facilitate access to a particular anatomic site, or may be formed from a stiff elastic material (e.g., polyurethane or latex) that may be bent by the clinician during use. In some embodiments, the delivery ends and/or elements are made of a shape-memory polymer such as a linear block copolymer of polyurethane, polyethylene terephthalate (PET) or polystyrene, or a thermoplastic material such as polyether ether ketone (PEEK).

Figure 2:
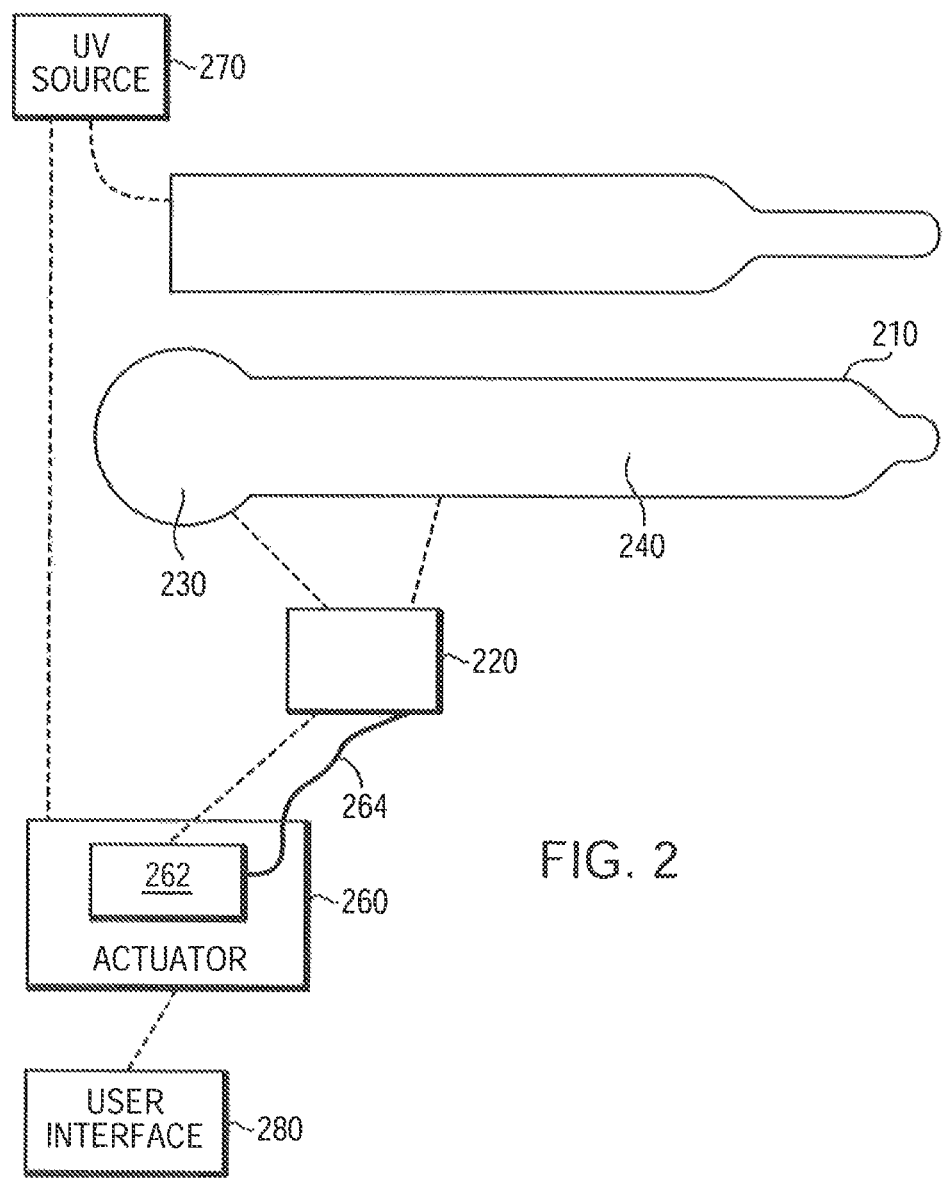
FIG. 2 schematically depicts a mechanical element and/or an actuator incorporated in the UV-activated riboflavin system in accordance with embodiments of the current invention.

Referring to FIG. 2, in various embodiments, the riboflavin solution applicator 210 incorporates a mechanical element 220 for generating pressure to drive the riboflavin solution from the reservoir 230 through the delivery element 240 to the target. The mechanical element may be, for example, a plunger, a pump (e.g., a peristaltic or electrolytic pump), a movable wall or other suitable fluid-driving component. In some embodiments, the mechanical element 220 is operated manually; the user may push a plunger, for example, in the manner of a syringe, or may operate the element 220 remotely via, for example, a stiff guide wire and handle. In other embodiments, a user-controlled actuator 260 directly controls the operation of the mechanical element 220, and the user operates the actuator 260 in a manner that does not require manual movement of a mechanical component.

For example, the actuator 260 may electromechanically or mechanically (e.g., using a handle 262 and a guide wire 264) operate a plunger-type forcing mechanism or electrically operate a pump and/or the UV light source 270. The actuator 260 is typically located on or within the applicator 210, and may be operated by means of a simple button or a more sophisticated user interface 280 that permits the user to specify a volume of riboflavin solution to be administered and/or a rate of administration. The user interface 280 may be part of the applicator 210 or may be remote therefrom, communicating in a wired or wireless manner with the actuator 260 by means of conventional transceiver circuitry. For example, the actuator 260 may be controlled by a computer, a smartphone, a tablet or other wireless devices that transmit signals thereto and, in some embodiments, receive feedback data therefrom.

The applicator 210 may be made of a flexible material or a rigid material, depending on the application. For example, in one embodiment, the applicator is rigid with a preformed shape designed to access a specific target region. In another embodiment, the delivery component 240 is flexible or articulated with an alterable shape that can be manipulated to access different anatomical targets that are difficult to access.

Figure 3A:
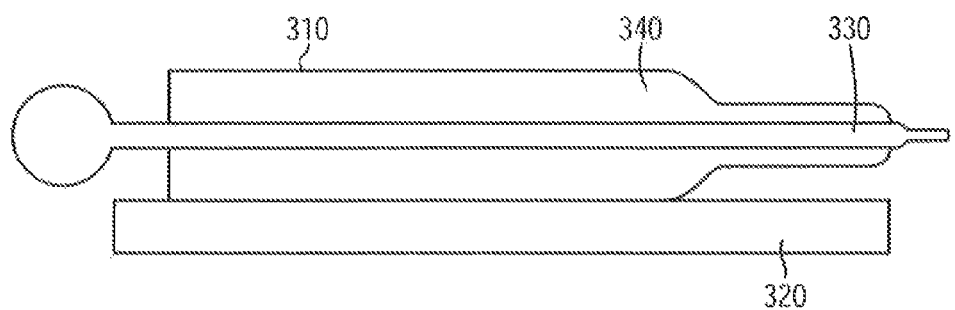
FIG. 3A schematically depicts the UV-activated riboflavin system integrated with a surgical instrument.
Figure 3B:
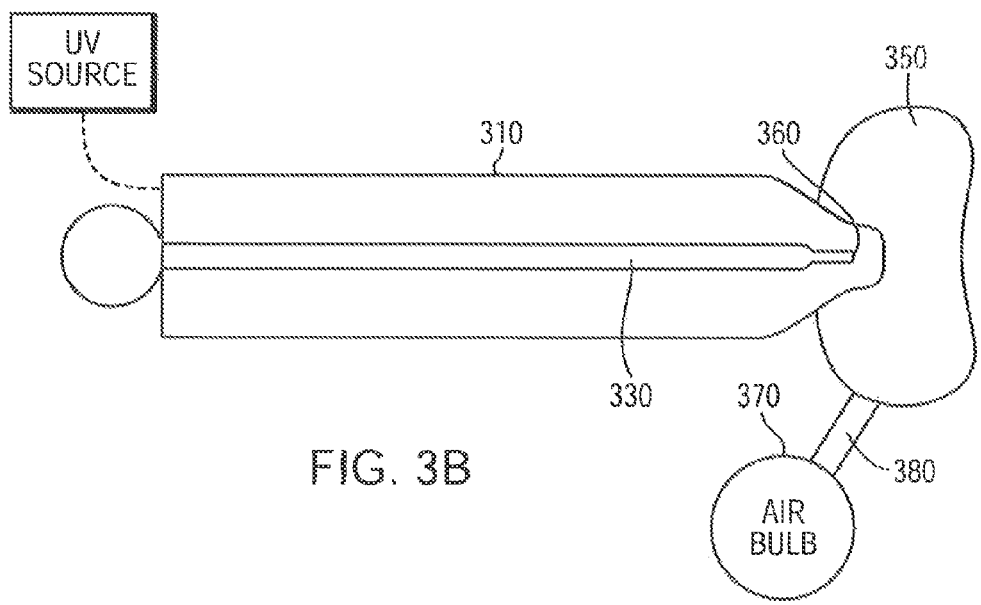
FIG. 3B schematically depicts an inflatable balloon incorporated in the UV-activated riboflavin system to help localize application of the riboflavin.

With reference to FIG. 3A, in some embodiments, the UV-activated riboflavin system 310 is integrated—i.e., attached to or joined to form a single structure—with an existing surgical or interventional instrument 320, e.g., a flexible or rigid endoscope. The endoscope may be, for example, one or more of a GI endoscope used in the esophagus, stomach, colon, GI tract or gastroenterology generally, a cystoscope used in the bladder or urology, a nasopharyngoscope used in the sinuses, nasal cavity, pharynx or ear, nose, and throat (ENT), a bronchoscope used in the lungs or pulmonology, an arthroscope used, for example, to place or examine orthopedic joints or in other orthopedic applications, a laparoscope used in intrabdominal procedures or other general surgeries, and/or a general endoscope used in oral cavity; the integration of each endoscope with the UV-activated riboflavin system is further described below. The UV light may be channeled through (1) a separate element attached to the endoscope, (2) optical elements of the endoscope itself, or (3) a completely independent optical delivery system resembling a flexible or rigid endoscope with the purpose of emitting UV light. Although the UV-activated riboflavin system 310 and the surgical instrument 320 are depicted in FIG. 3A in the form of a single handheld wand, one of ordinary skill in the art will understand that the riboflavin solution applicator 330 and the UV light-emitting device 340 thereof may be separate, and the surgical instrument 320 may be integrated with either or both of the applicator 330 and the UV light-emitting device 340; for example, the components 330, 340 may separately attach to the body of the instrument 320. The UV light-emitting device 340 may also be combined with, e.g., an articulating shaver to create a combined system for surgical debridement together with the riboflavin and UV light technique. With reference to FIG. 3B, in some embodiments, the UV-activated riboflavin system 310 incorporates a translucent, inflatable balloon 350 to help localize application of the riboflavin and may also be used in connection with related surgical procedures for treating the target region. The inflatable balloon 350 may be positioned adjacent or proximal to the orifice 360 of the riboflavin solution applicator 330. For example, the balloon 350 may surround the system 310 (e.g., inflating to a torus) such that the applicator orifice extends beyond it; in this way, the balloon forms a dam that may completely block the lumen of an anatomical passage, preventing dispersal of the riboflavin solution. In some embodiments, the balloon 350 is inflated using a hand-held air bulb 370, for example, which is fluidly connected to the balloon 350 by a tube 380 running along or within the system 310 or the applicator 330. In other embodiments, the balloon is inflated by command of the actuator 260 (see FIG. 2), which triggers operation of pump. For example, the pump may be the same pump that causes delivery of riboflavin solution through the orifice 360, but selectively channeled to alternately operate the balloon 350 or the fluid-forcing mechanism.

During operation, a riboflavin-containing solution may first be applied to a target region; the target region is then exposed to the UV light for a period of time to activate the riboflavin. As further described below, this technique may be carried out as a stand-alone procedure performed in an office or an operating room setting; it may also be performed in conjunction with a variety of other surgical procedures.

Combination of a GI Endoscope with the UV-Activated Riboflavin System

Figure 4A:
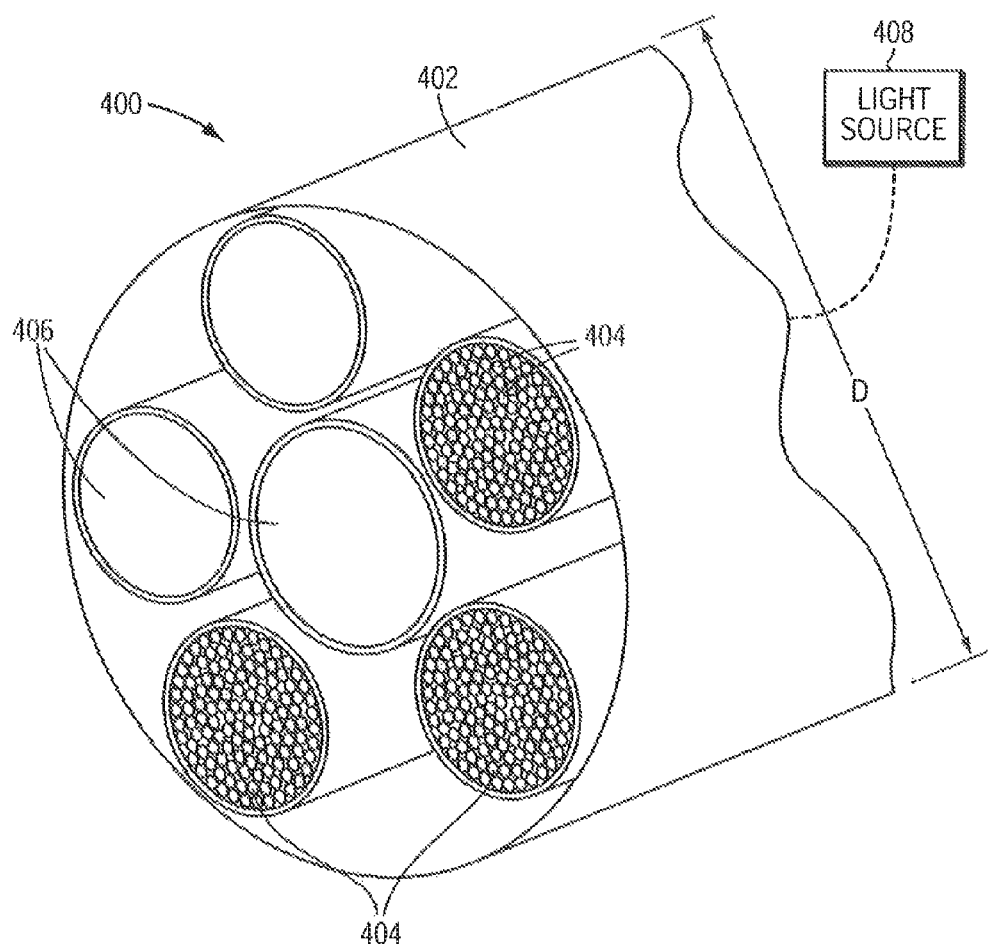
FIG. 4A is a cross sectional view of a gastrointestinal endoscope.

GI tract infections are relatively common in humans and animals and may be caused by any number of pathogens (e.g. rotavirus, *E. coli*, or *campylobacter*). A GI endoscope has been long used in examining the GI diseases. Referring to FIG. 4A, the GI endoscope 400 typically includes a catheter 402 having optical fibers 404 and multiple long, narrow working channels 406; the overall outer diameter D ranging from 5 mm to 15 mm is constrained by the limited dimensions of the body cavity opening (e.g., throat, intestine, trachea). The working channels 406 may include air and/or water channels that provide an airtight or watertight internal compartment integrated through all components for electrical wiring and controls, thereby protecting the components from exposure to patient secretions during use as well as facilitating submersion of the endoscope for cleaning and subsequent disinfection. In addition, the GI endoscope may include a light source (such as a light-emitting diode (LED), a halogen light source, or a metal halide light source) 408 that emits light via the optical fibers 404 to the distal (insertion) end of the catheter 402.

Figure 4B:
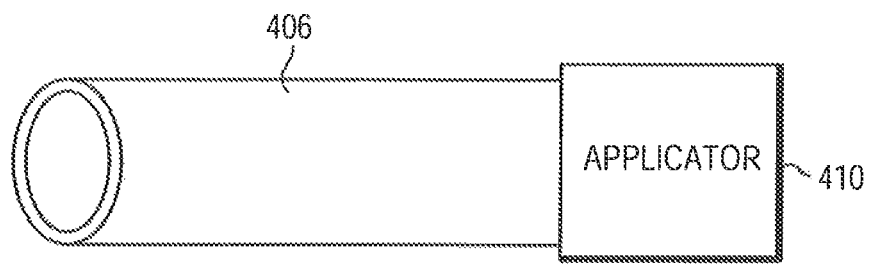
FIGS. 4B-4F schematically depict the UV-activated riboflavin system integrated with the gastrointestinal endoscope in accordance with various embodiments of the invention.
Figure 4C:
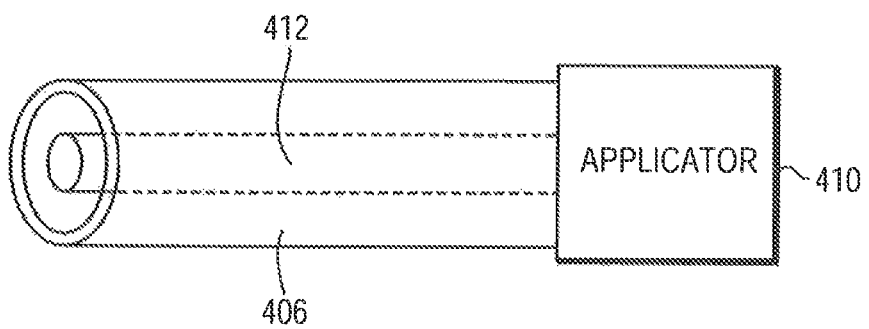
Figure 4D:
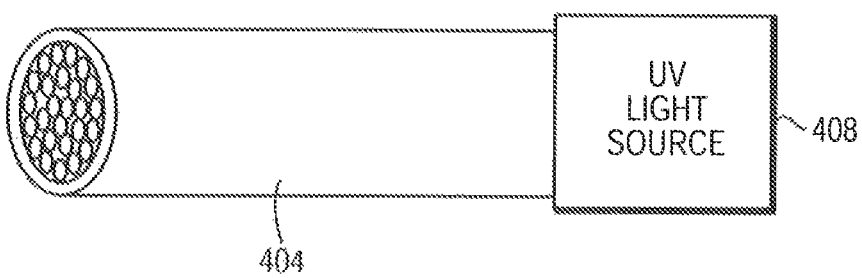
Figure 4E:
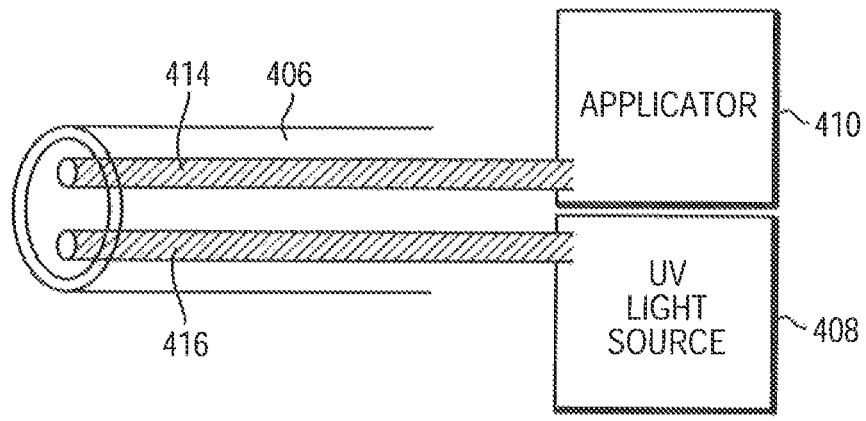
Figure 4F:
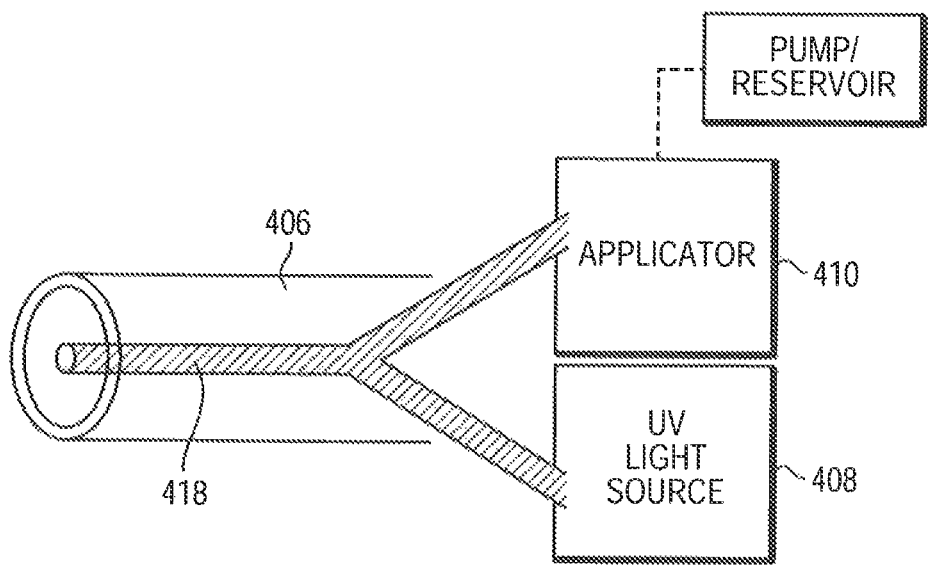

Referring to FIG. 4B, in various embodiments, at least one working channel 406 is directly connected to a riboflavin solution reservoir and applicator 410 to facilitate application of a riboflavin-containing solution to a target region in the GI tract. Alternatively, as shown in FIG. 4C, the riboflavin solution applicator 410 may include a catheter 412 that can be inserted into the working channel 406 for delivering the riboflavin-containing solution. With reference to FIG. 4D, in one embodiment, the light source 408 includes or consists of a UV light source that transmits UV light via one or more optical fibers inserted into the working channel 406 to activate riboflavin, thereby combating the pathogens at the target region. In another embodiment, the riboflavin solution and UV light are guided to the target region using separate delivery channels 414, 416, both confined within a working channel 406 (i.e., less than 4 mm); this allows the UV-activated riboflavin system to be supplied in the form of a kit that can be easily applied to and removed from the GI endoscope 400 (FIG. 4E). In some embodiments, the riboflavin solution and UV light are delivered through a single optofluidic channel 418 (FIG. 4F). For example, the riboflavin solution and UV light may be delivered to the infected or at-risk area at different times, in a pulsed mode of operation, whereby alternating pulses of riboflavin solution and UV light are applied to the treatment area for a predetermined time. The pulses may be of equal length or may be adjusted to provide flexible treatment options. As described above, the riboflavin is generally supplied to the target region in the GI tract by a pump connected to a riboflavin solution reservoir; the pressure provided by the pump may be adjusted to suit a particular patient or particular treatment mode. The channel(s) that deliver the riboflavin solution and UV light may be made of flexible material to provide bending capability when passing through the GI tract. Accordingly, the combined GI endoscope 400 with the UV-activated riboflavin system enables a physician to diagnose GI diseases while providing an instant treatment.

Combination of a Cystoscope with the UV-Activated Riboflavin System

Figure 5A:
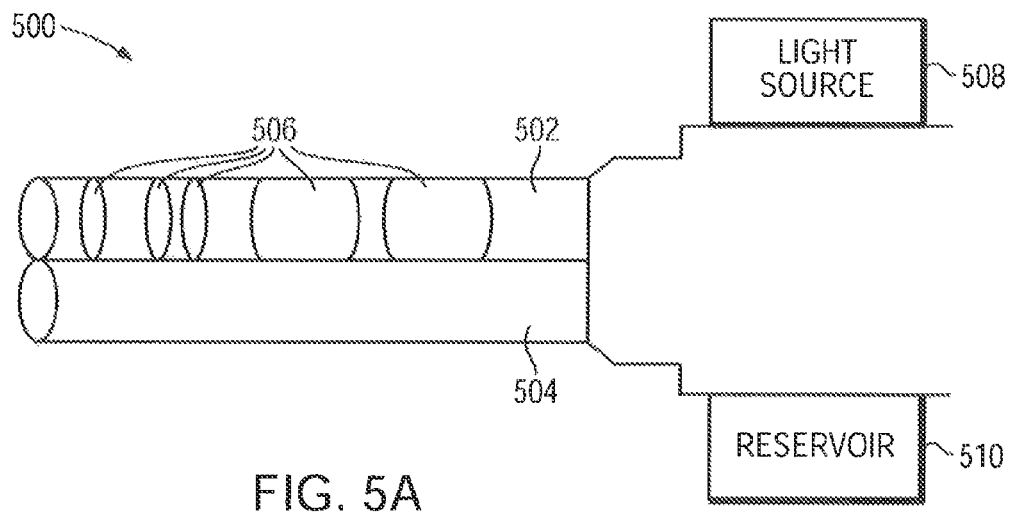
FIG. 5A is a sectional view of a cystoscope.

Referring to FIG. 5A, a cystoscope 500 is a long, thin telescope-like instrument that enables a urologist to look into the patient's bladder and diagnose abnormalities as well as to adjust the positioning of the ureters. The cystoscope 500 typically includes two channels 502, 504; the first optical channel 502 consists essentially of a lens assembly 506 and a light source 508 to provide images inside the bladder and urethra, whereas the second fluidic channel 504 allows fluids stored in the reservoir 510 to be delivered into the bladder. Generally, the cystoscope is small enough (e.g., approximately 5 mm) to be inserted through the urethra into the bladder.

Figure 5B:
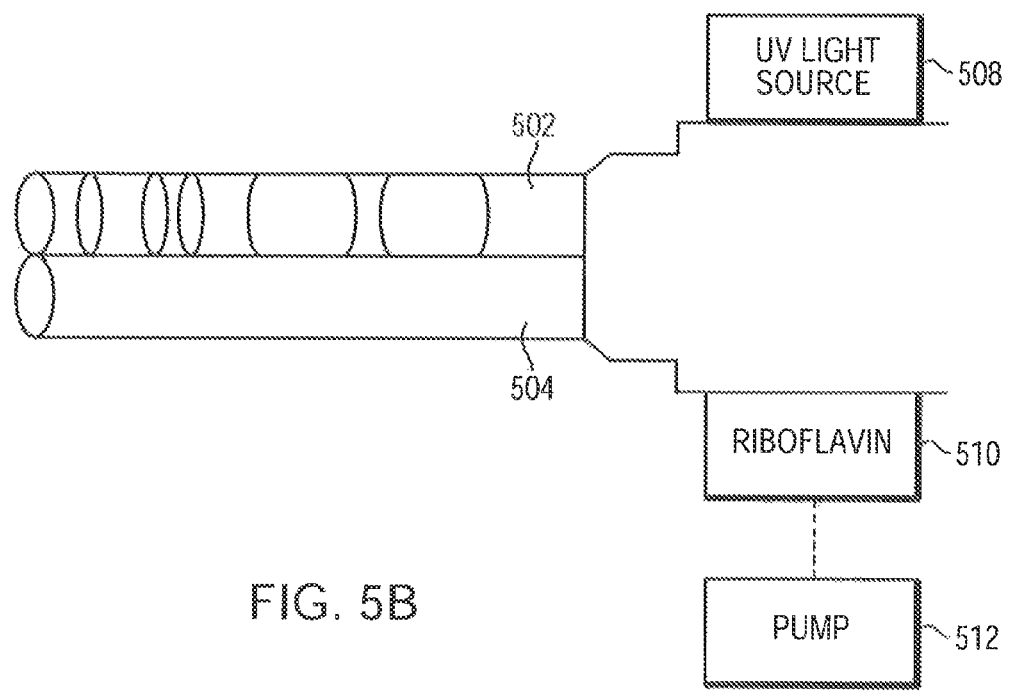
FIGS. 5B-5D schematically depict the UV-activated riboflavin system integrated with the cystoscope in accordance with various embodiments of the invention.
Figure 5C:
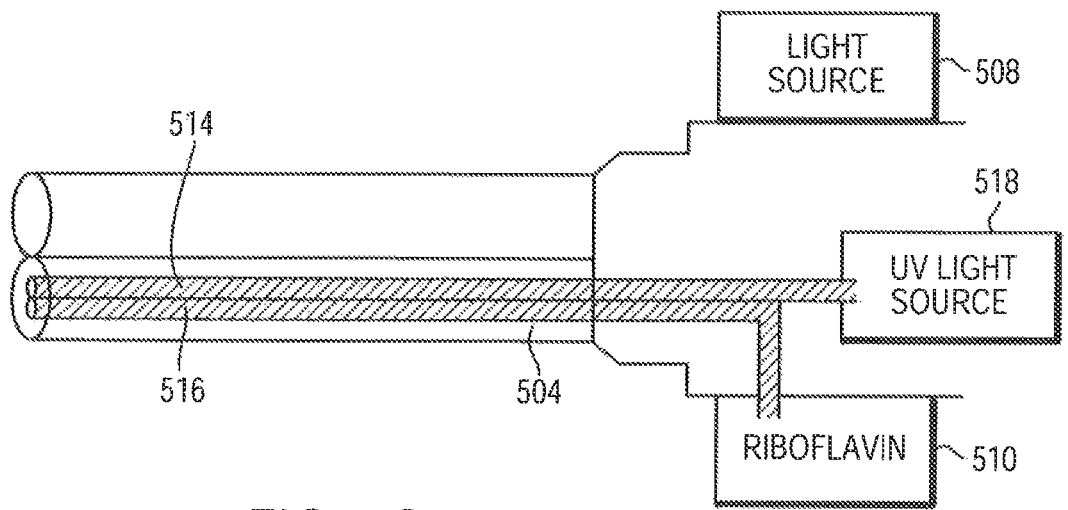
Figure 5D:
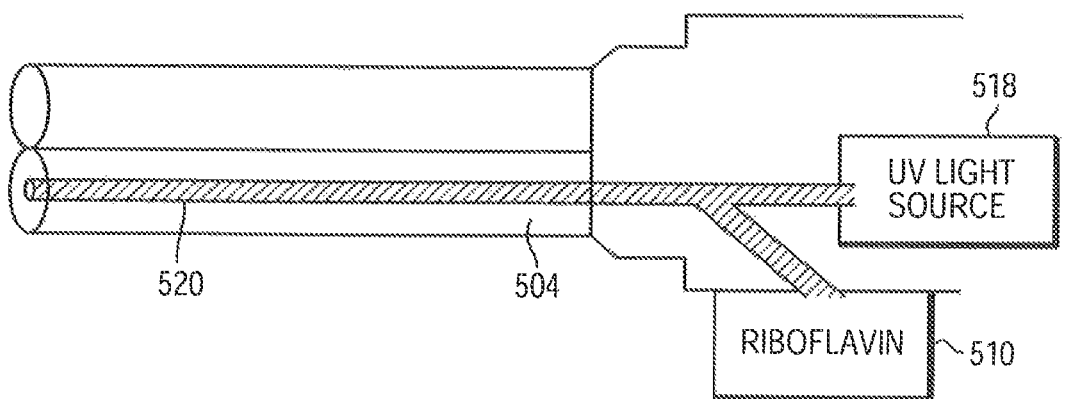

Referring to FIG. 5B, in various embodiments, the riboflavin solution may be stored in the riboflavin reservoir 510 prior to being applied to a target region in the urethra or bladder. In addition, the light source 508 includes a UV light source that transmits UV light to the target region via the optical channel 502. In operation, the combined cystoscope and UV-activated riboflavin system may first deliver the riboflavin solution to the target site using, for example, a pump 512, and subsequently the system emits UV light to activate the delivered riboflavin to combat pathogens; this approach is effective in treating, for example, a urinary tract infection or a bladder infection. In some embodiments, the bladder is first distended or stretched with a pressurized riboflavin solution; subsequent application of UV light guided by the optical channel 502 can treat infections throughout the entire bladder and/or urinary tract. Because the UV-activated riboflavin treatment can utilize the existing channels of the cystoscope, the integrated system can provide cost-effective treatments for pathogenic infections. In another embodiment, illustrated in FIG. 5C, the channel 514 that guides the UV light and the channel 516 that delivers the riboflavin solution both pass through the fluid channel 504. In addition, the riboflavin solution and UV light may be delivered through a single optofluidic channel 520 (FIG. 5D); this combination, again, allows the UV-activated riboflavin system to be supplied in the form of a kit that can be removably integrated with the cystoscope 500. In one implementation, the channel(s) is made of rigid or flexible material that can be inserted into the fluid channel 504 of the cystoscope 500.

Combination of a Nasopharyngoscope with the UV-Activated Riboflavin System

Figure 6A:
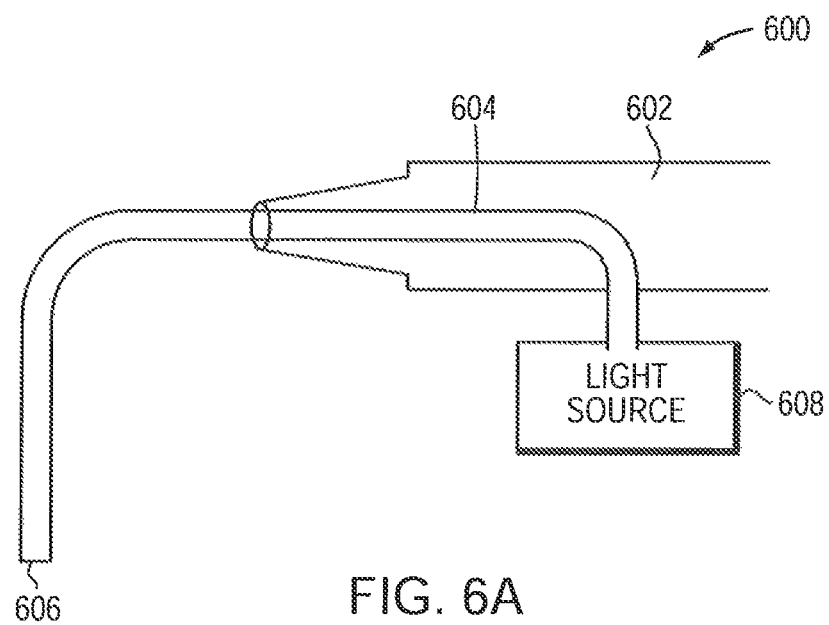
FIG. 6A is a sectional view of a nasopharyngoscope.
Figure 6B:
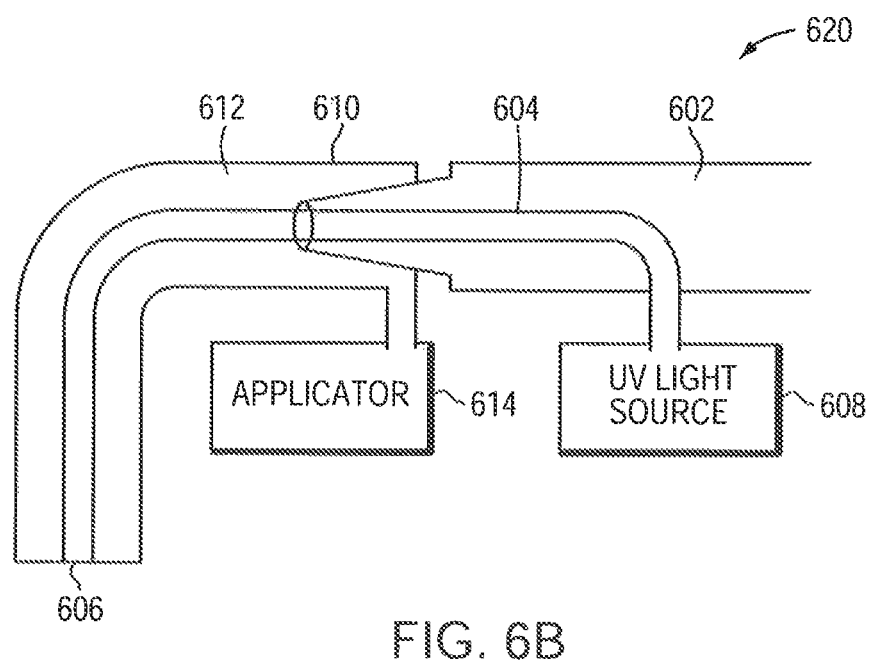
FIG. 6B schematically depicts the UV-activated riboflavin system integrated with the nasopharyngoscope in accordance with an embodiment of the invention.

A nasopharyngoscope provides a direct view of every part of the upper respiratory tract from the nasal passages down the throat to the larynx. Referring to FIG. 6A, the nasopharyngoscope 600 typically includes a main body portion 602, optical fibers 604 extending from the body portion 602 to the distal end 606, and a light source 608 emitting light to the distal end via the optical fibers 604 for imaging a target region. Referring to FIG. 6B, in various embodiments, the nasopharyngoscope 600 includes a flexible sleeve 610 covering at least a portion of the extended optical fibers 604. The channel 612 between the sleeve 610 and the optical fibers 604 may be used to deliver the riboflavin solution from the applicator and reservoir 614. In operation, the distal end 606 of the combination device 620 may be inserted into various paranasal sinus cavities (e.g., sinus maxillaris, sinus frontalis, or sinus sphenoidalis) for examination of the target region (e.g., the paranasal sinus cavity or the walls of the cavity). Upon detection of pathogenic infections, the riboflavin solution applicator 614 first delivers the riboflavin solution to the distal end; the light source 608 may then transmit UV light to activate riboflavin, thereby combating pathogens at the target region. In addition, this combined device 620 may be utilized in a variety of paranasal sinus procedures (e.g., functional endoscopic sinus surgery or post-surgical debridement of the paranasal sinus cavities) to effectively prevent infections. In some embodiments, the UV light may be delivered to the distal end by a fiber separate from the extended optical fibers 604.

Combination of a Bronchoscope with the UV-Activated Riboflavin System

Figure 7A:
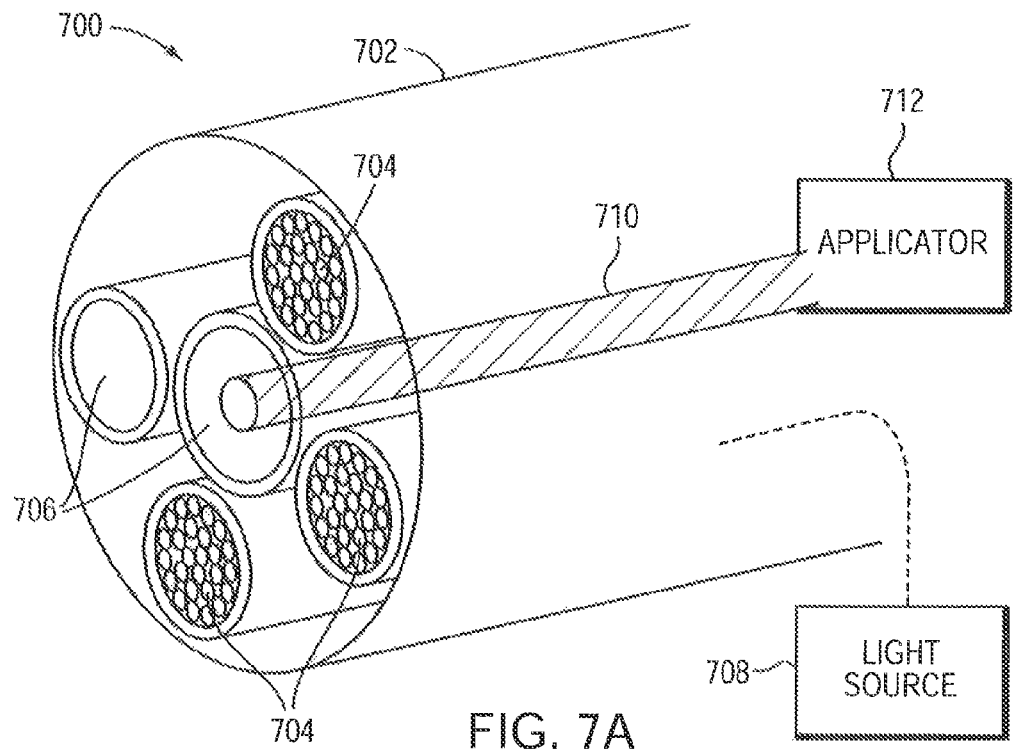
FIGS. 7A-7B schematically depict the UV-activated riboflavin system integrated with a bronchoscope in accordance with various embodiments of the invention.
Figure 7B:
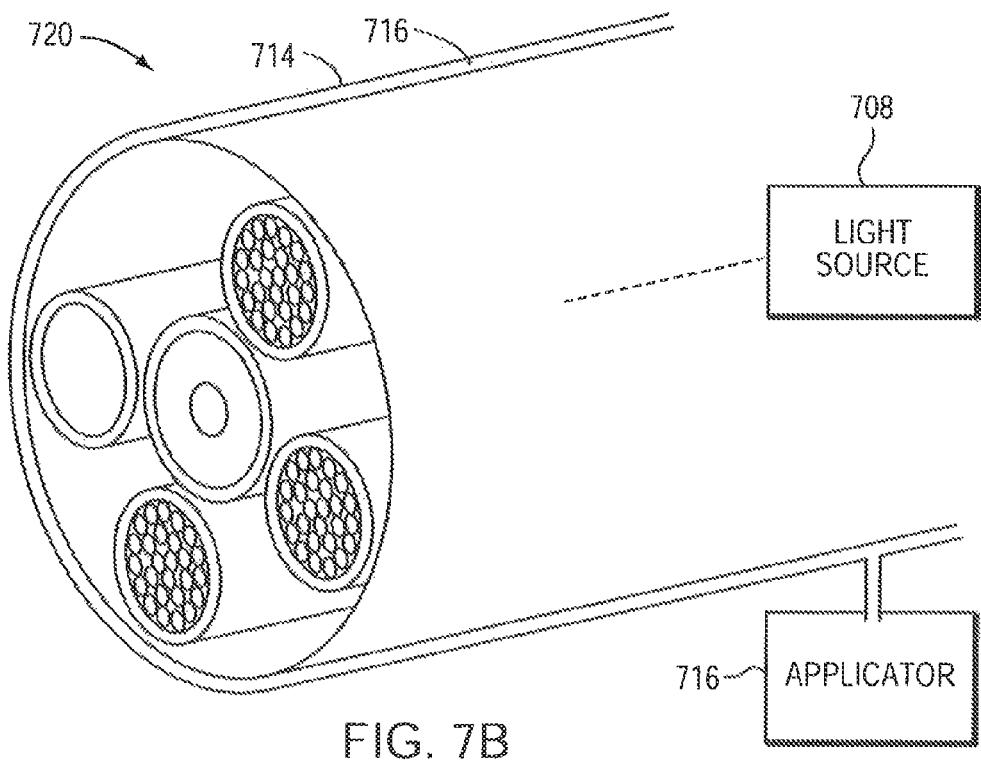

A bronchoscope is insertable into a patient's airways (e.g., lungs), usually through the nose or mouth, allowing a physician to examine the patient's airways for abnormalities, such as bleeding, tumors, or inflammation. Referring to FIG. 7A, the bronchoscope 700 has a structure similar to the GI endoscope, including a catheter 702 that contains optical fibers 704 and multiple long narrow lumens 706 for allowing therapeutic approaches, such as electrocautery. There are two types of bronchoscope 700, a rigid bronchoscope having relatively large lumens and a flexible bronchoscope having relatively narrow (i.e., small-diameter) lumens. In addition, the bronchoscope includes a light source 708 for emitting light via the optical fibers 704 to the distal end of the insertion catheter 702. Because of the similarity between the bronchoscope 700 and the GI endoscope, the bronchoscope 700 may be combined with the UV-activated riboflavin system in a manner similar to the combined GI endoscope and UV-activated riboflavin system as described above to treat, for example, pneumonia, pneumonitis, bronchitis, or other lung infections. For example, the light source 708 may provide UV light to activate a riboflavin solution delivered to a target region by a fluid channel 710 from an applicator 712; the fluid channel 710 may be inserted into the lumen 706 of the bronchoscope 700. In addition, referring to FIG. 7B, because the bronchoscope 700 is typically smaller (having an outer diameter of 5 mm) than the GI endoscope, in various embodiments, a sleeve 714 is applied to the outer surface of the bronchoscope 700. As a result, a channel 716 between the sleeve 714 and the outer surface of the bronchoscope 700 may be used to deliver the riboflavin solution from the applicator 716. The sleeve 714 may be made of a rigid or flexible material that allows the integrated device 720 to be inserted through the patient's airways.

Combination of an Arthroscope with the UV-Activated Riboflavin System

Figure 8A:
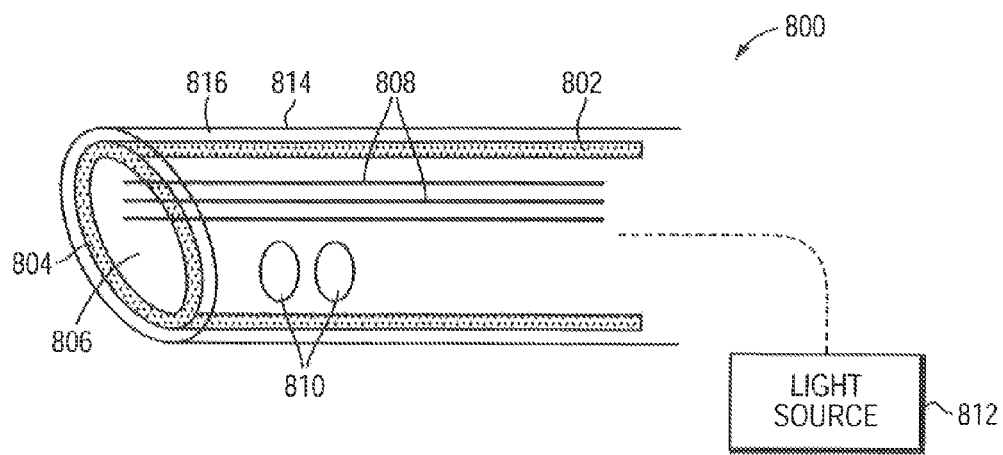
FIG. 8A is a sectional view of an arthroscope.

An arthroscope can deliver images of an operating region inside or near a joint or joint space of a patient while the same or another instrument performs a surgical procedure (e.g., joint replacement, orthopedic implantation, or post-operative treatment for infections) in the operating region. Referring to FIG. 8A, the arthroscope 800 includes a trocar 802 surrounded by a rigid tube 804; the trocar 802 has a lumen 806, in which an optical system, such as optical fibers 808 or a lens assembly 810, may guide light emitted by a light source 812 to the operative field in the joint or joint space. In addition, the arthroscope 800 may include an atraumatic sheath 814 made of, for example, a disposable polymer or disposable metal to protect the arthroscope. The atraumatic sheath 814 may include an aperture in the distal end for interstitial tissue drainage, or fluid irrigation; the interstitial tissue or fluid may be vacuumed out from the joint space via the channel 816 created between the sheath 814 and the outer surface of the tube 804.

Figure 8B:
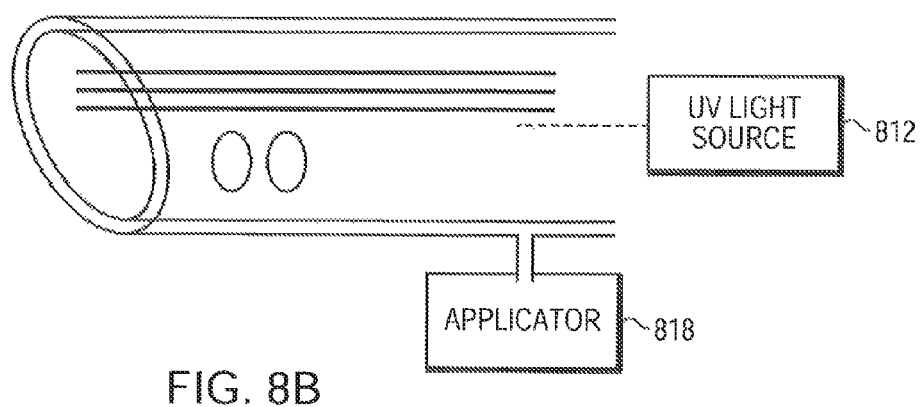
FIGS. 8B-8D schematically depict the UV-activated riboflavin system integrated with the arthroscope in accordance with various embodiments of the invention.
Figure 8C:
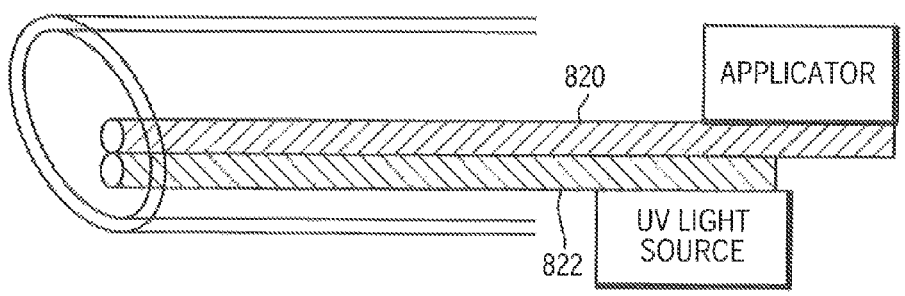
Figure 8D:
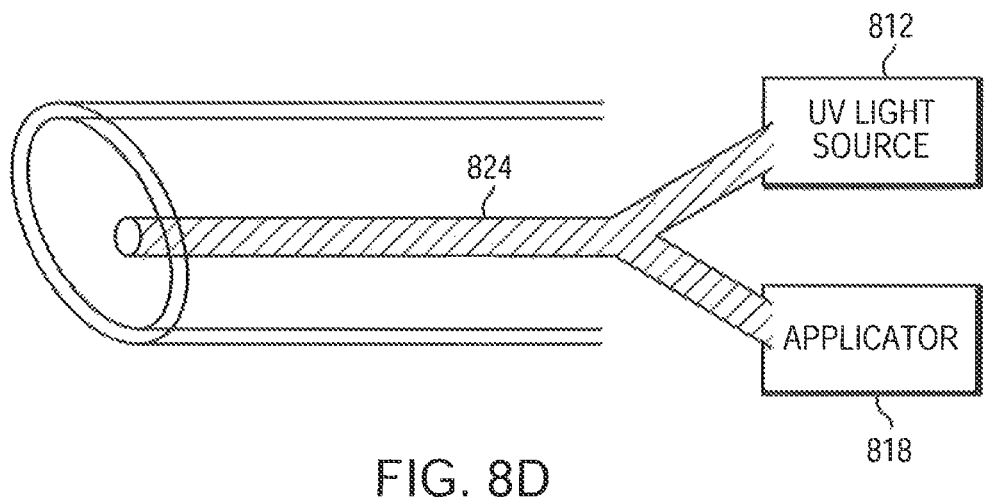

The arthroscope may be combined with the UV-activated riboflavin system to sanitize a newly placed orthopedic implant or to treat infections of the joint or tissue in the joint space. For example, with reference to FIG. 8B, the fluidic channel 816 may be connected to a riboflavin applicator 818 and the light source 812 may include a UV light source. In various embodiments, following placement of an implant, the operative region is first flooded with riboflavin solution delivered by the applicator 818; the operative region is then irradiated indiscriminately with UV light. Riboflavin solution in the applicator may be, for example, sprayed or aerosolized broadly across the entire operative region to ensure coating of the implant. In addition, the UV light may be capable of irradiating the entire region at once or specific areas of the implant selectively. Referring to FIG. 8C, in another embodiment, the riboflavin solution and UV light are guided to the operative region using separate delivery channels 820, 822, both dimensioned to fit within the lumen 806. In still another embodiment, the riboflavin solution and UV light are delivered through a single optofluidic channel 824 (FIG. 8D). Again, the combined systems depicted in FIGS. 8C and 8D allow the UV-activated riboflavin system to be supplied in the form of a kit that can be easily added to or removed from the integrated arthroscope 800. The combined arthroscope and UV-activated riboflavin system provides facilitates treating pathogenic infections of the joint or the joint space prophylactically during joint surgery or a joint replacement procedure. Additionally, the combined system is capable of treating post-operative infections of the joint or orthopedic implants as well as providing a primary therapy to any non-surgery related joint infections.

Combination of a Laparoscope with the UV-Activated Riboflavin System

Figure 9A:
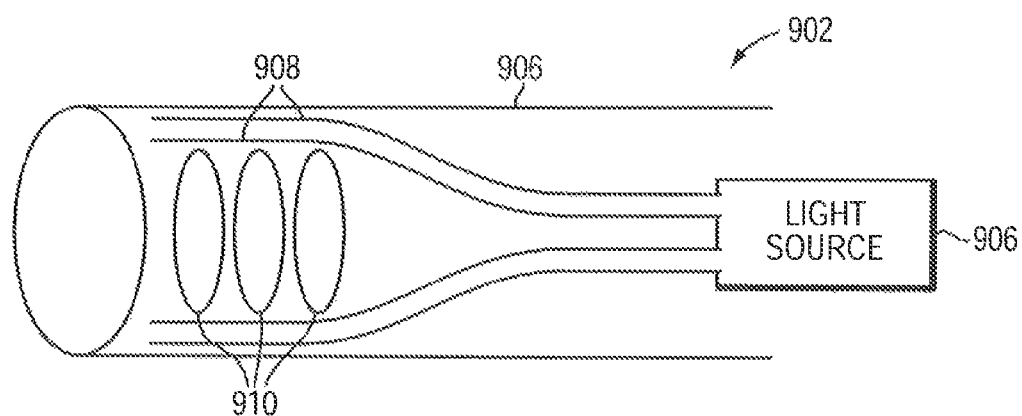
FIGS. 9A and 9B are sectional views of a video-laparoscope and a laser-laparoscope, respectively.
Figure 9B:
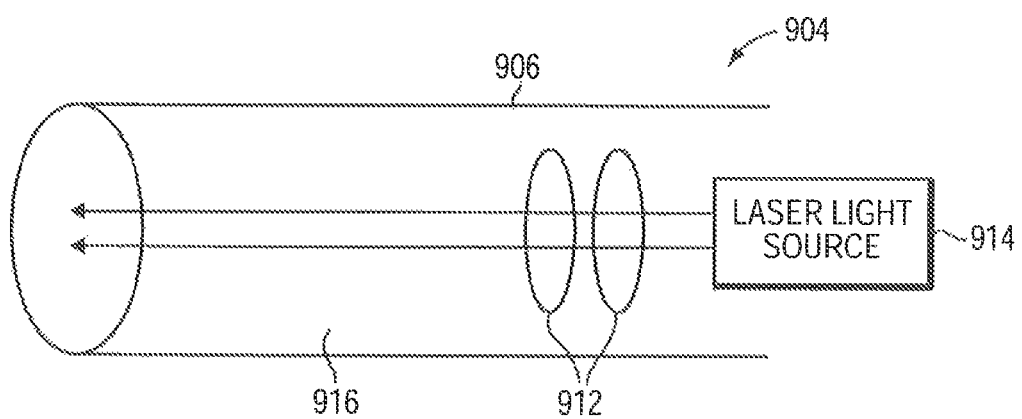

A laparoscope allows surgeons to perform complex surgeries in the abdomen or pelvis via small incisions (usually, 0.5-1.5 cm), thereby shortening patients' recovery times. FIGS. 9A and 9B illustrate two types of laparoscope, namely, a video-laparoscope 902 and a laser-laparoscope 904, both of which include a trocar 906 insertable into the human body. The video-laparoscope includes a light source 906 emitting light to the operative site using, for example, optical fibers 908 and/or a lens assembly 910; images of the operative site can then be captured by a video camera (not shown). The laser-laparoscope 904 includes a lens assembly 912 that can guide laser beams emitted from the laser light source 914 through the inner lumen 916 to the operative site.

Figure 9C:
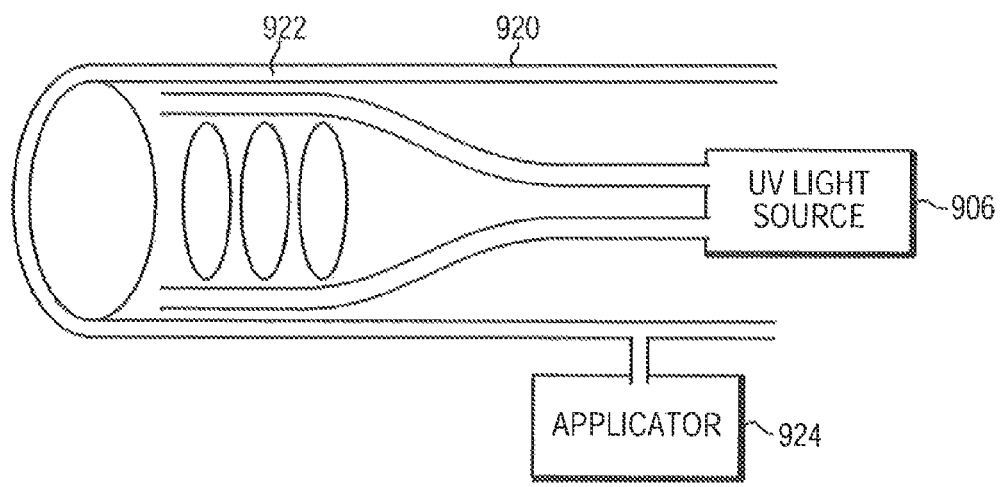
FIGS. 9C-9G schematically depict the UV-activated riboflavin system integrated with the video-laparoscope and the laser-laparoscope in accordance with various embodiments of the invention.
Figure 9D:
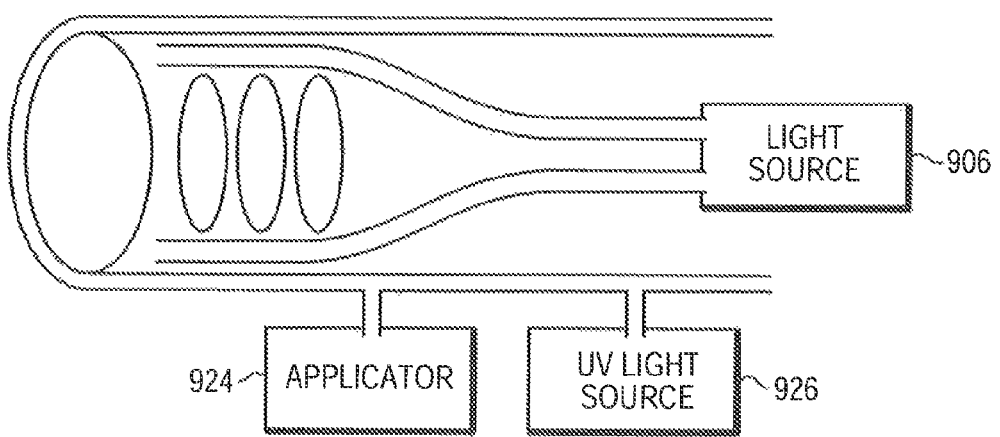
Figure 9E:
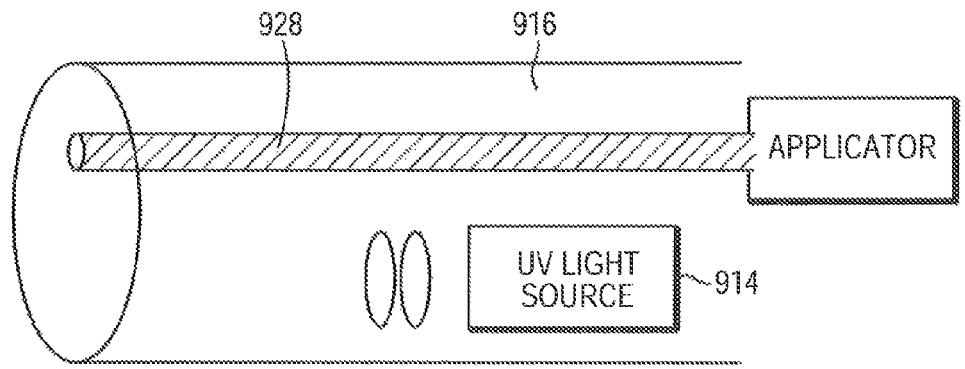
Figure 9F:
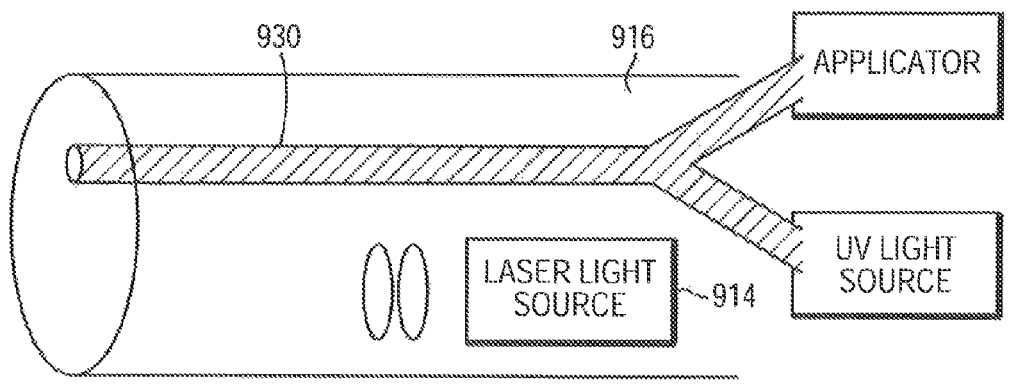
Figure 9G:
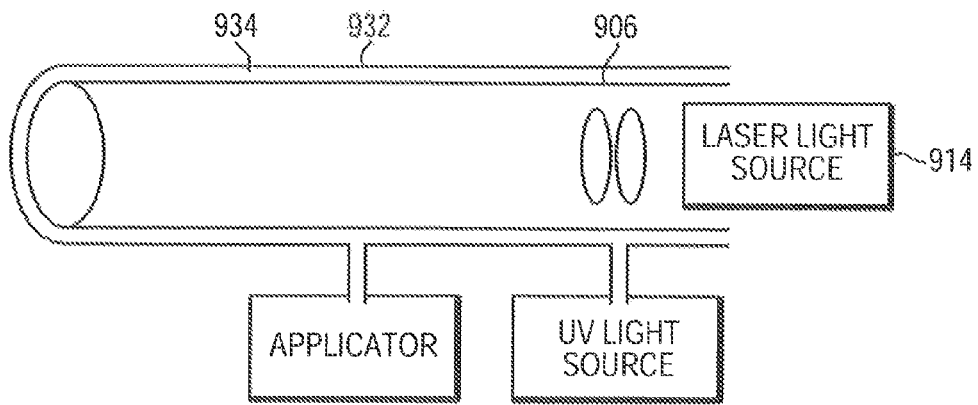

Both video-laparoscope 902 and laser-laparoscope 904 may be integrated with the UV-activated riboflavin system to treat or prevent maladies caused by pathogenic microorganisms. For example, with reference to FIGS. 9C and 9D, the video-laparoscope 902 may include a sleeve 920 surrounding the trocar 906 to create a fluidic channel 922 therebetween. Upon applying the riboflavin-containing solution from the applicator 924 to the operative regions (e.g., peritoneum or tissues in the peritoneal or thoracic cavity), the light source 906 and/or an external UV light source 926 may transmit UV light to irradiate the target regions, thereby interfering with the pathogens' ability to proliferate. Referring to FIG. 9E, in various embodiments, the UV-activated riboflavin system, including a channel 928 is inserted into the lumen 916 of the laser-laparoscope 904 for applying the riboflavin solution to the target. Again, UV light for activating the riboflavin may be emitted from the light source 914 and delivered to the target via the lumen 916. In another embodiment, an optofluidic channel 930 may be utilized to deliver both riboflavin solution and UV light to the target (FIG. 9F). In addition, similar to the integrated video-laparoscope, a sleeve 932 may cover the outer surface of the trocar 906 to create a fluidic channel 934 that is capable of delivering the riboflavin solution and UV light concurrently or subsequently to the target regions (FIG. 9G).

Combination of a Dental Instrument with the UV-Activated Riboflavin System

Figure 10A:
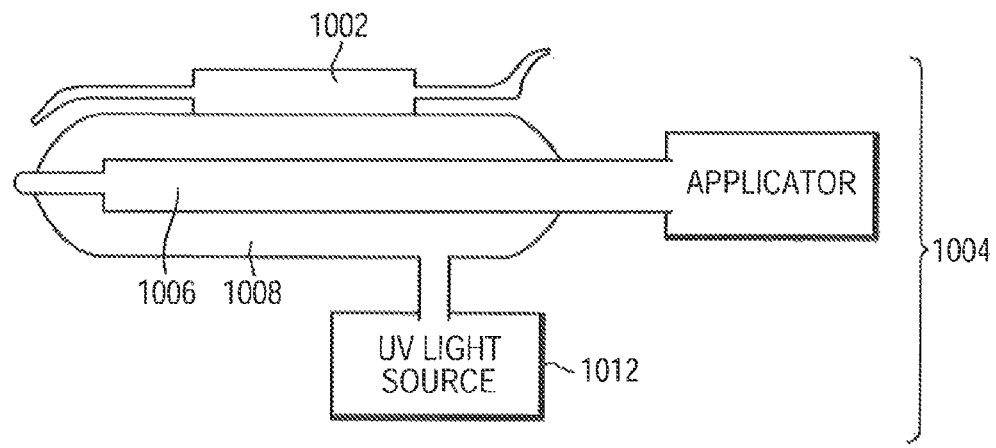
FIGS. 10A and 10B schematically depict the UV-activated riboflavin system integrated with a dental instrument in accordance with various embodiments of the invention.
Figure 10B:
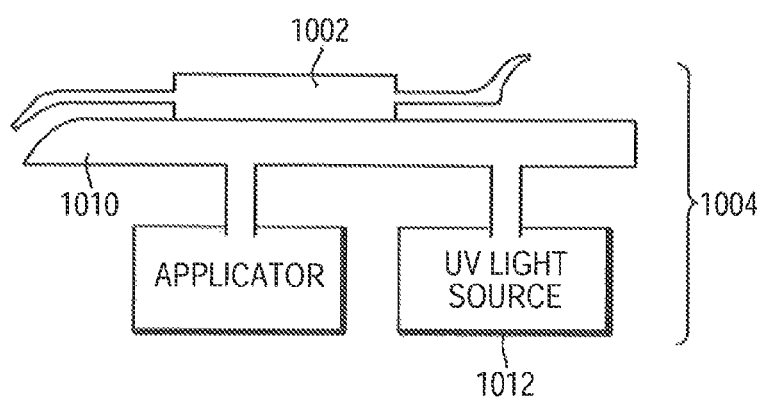

Referring to FIG. 10, in various embodiments, the dental instrument 1002 (such as a carver, scraper, microspatula, or mirror) is attached to or joined to the UV-activated riboflavin system 1004 to form a single device. Again, the riboflavin solution and UV light may be delivered in separate channels 1006, 1008 or a same channel 1010. The integrated dental instrument may treat or prevent infections caused by dental surgeries. In addition, a riboflavin solution that contains a dental formulation (e.g. toothpaste or oral rinse) may be applied to the dentition or periodontal tissues; a UV light-emitting device configured for oral usage may then be utilized to irradiate the riboflavin applied in the oral cavity and/or on the dental structures for treating the infections.

Accordingly, the present invention provides systems and methods to integrate the UV-activated riboflavin system with various endoscopes, thereby producing a globally or locally acting antimicrobial effect on the surface that is internal to the anatomy and sequentially exposing the riboflavin to UV light. The riboflavin may be applied via use of a riboflavin-containing solution, paste, lotion, cream, gel, an additive to a rinse solution, toothpaste, or other topical pharmacologic products. Because this technique can effectively reduce the proliferation rate of infectious pathogens without complications or side effects associated with the systemic delivery of antimicrobials, this technique may be inexpensively and broadly applied to various diseases caused by pathogen infections.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for examining an internal anatomical target in a patient's body and treating pathogenic infections therein, the system comprising:
   an endoscope comprising at least one optical channel for examining the internal anatomical target;
   a device for delivering actinic radiation, the radiation-delivery device comprising a UV radiation source and an emission channel that is optically separate from the at least one optical channel;
   an applicator comprising a reservoir for a radiation-activatable biocidal fluid having a riboflavin solution or a riboflavin-derivative solution and a fluidic channel; and
   an inflatable balloon positioned proximal to an orifice of the applicator for localizing application of the radiation-activatable biocidal fluid;
   wherein a light output of the emission channel and a fluidic outlet of the fluidic channel are configured for accessing the internal anatomical target and delivering actinic radiation and a radiation-activatable biocidal fluid, respectively, thereto without interfering with operation of the endoscope.

2. The system of claim 1, wherein the endo scope, device and the applicator are integrated into a single assembly.

3. The system of claim 1, wherein the endoscope is configured to enter a first surgical port and the light output and the fluidic outlet are configured to enter a second surgical port spaced apart from the first surgical port.

4. The system of claim 1, wherein the endoscope is a gastrointestinal endoscope, comprising at least one working channel, the at least one optical channel guiding light to the internal anatomical target.

5. The system of claim 4, wherein the working channel is the fluidic channel and the optical channel is the emission channel.

6. The system of claim 4, wherein the emission channel and the fluidic channel are disposed within the working channel of the gastrointestinal endoscope.

7. The system of claim 1, wherein the endoscope is a cystoscope, comprising a first channel for providing images of the internal anatomical target and a second channel for allowing fluids to be instilled into the internal anatomical target.

8. The system of claim 7, wherein the first channel is the emission channel and the second channel is the fluidic channel.

9. The system of claim 7, wherein the emission channel and the fluidic channel are inserted in the second channel of the cystoscope.

10. The system of claim 1, wherein the endoscope is a nasopharyngoscope, the at least one optical channel guiding light to the internal anatomical target.

11. The system of claim 10, further comprising a sleeve surrounding at least a portion of the nasopharyngoscope, wherein a channel created between the sleeve and an outer surface of the nasopharyngoscope is the fluidic channel and the optical channel is the emission channel.

12. The system of claim 10, further comprising a sleeve surrounding at least a portion of the nasopharyngoscope, wherein a channel created between the sleeve and an outer surface of the nasopharyngoscope is the fluidic channel and the emission channel.

13. The system of claim 1, wherein the endoscope is a bronchoscope, comprising at least one working channel.

14. The system of claim 13, wherein the working channel is the fluidic channel and the optical channel is the emission channel.

15. The system of claim 13, wherein the emission channel and the fluidic channel are inserted in the working channel of the bronchoscope.

16. The system of claim 1, wherein the endoscope is an arthroscope, comprising a trocar having a lumen for guiding light to the internal anatomical target.

17. The system of claim 16, wherein the emission channel and the fluidic channel are inserted in the lumen of the trocar.

18. The system of claim 16, further comprising a sleeve surrounding at least a portion of the trocar, wherein a channel created between the sleeve and an outer surface of the arthroscope is the fluidic channel and the emission channel.

19. The system of claim 1, wherein the endoscope is a laparoscope, comprising a trocar having an optical channel for guiding light to the internal anatomical target.

20. The system of claim 19, further comprising a sleeve surrounding at least a portion of the trocar, wherein a channel created between the sleeve and an outer surface of the laparoscope is the fluidic channel and the optical channel is the emission channel.

21. The system of claim 19, further comprising a sleeve surrounding at least a portion of the trocar, wherein a channel created between the sleeve and an outer surface of the laparoscope is the fluidic channel and the emission channel.

22. The system of claim 19, wherein the emission channel and the fluidic channel are inserted in the optical channel of the trocar.

23. The system of claim 1, further comprising a supply of the radiation-activatable biocidal fluid in the fluid reservoir for delivery to the internal anatomical target via the fluidic channel.

24. A method for examining an internal anatomical target in a patient's body and treating pathogenic infections therein, the method comprising:
- inserting an endoscope comprising at least one optical channel adjacent to or into the internal anatomical target;
- capturing an image of the target via the at least one optical channel of the endo scope;
- while capturing the image and without interfering therewith, delivering a radiation-activatable biocidal fluid comprising a riboflavin solution or a riboflavin-derivative solution to the target;
- inflating a balloon for localizing application of the radiation-activatable biocidal fluid; and
- exposing the target to actinic radiation comprising a UV radiation via an emission channel to activate the radiation-activatable biocidal fluid, the emission channel being optically separate from the at least one optical channel.

25. The method of claim 24, wherein the actinic radiation is UV radiation.

26. The method of claim 24, wherein the radiation-activatable biocidal solution comprises a riboflavin solution or a riboflavin-derivative solution.

* * * * *